United States Patent [19]

Germanaud et al.

[11] Patent Number: 5,062,977
[45] Date of Patent: Nov. 5, 1991

[54] SULPHUR-CONTAINING ADDITIVES TO LUBRICANTS WITH ANTIWEAR AND EXTREME-PRESSURE EFFECT AND THE PROCESSES FOR THEIR PREPARATION AND COMPOSITIONS CONTAINING THE SAID ADDITIVES

[75] Inventors: Laurent Germanaud, Valencin Le Fayet; Patrick Azorin, La Plaine - Mornant; Lhopital Michel, Francheville, all of France

[73] Assignee: Elf France, Courbevoie, France

[21] Appl. No.: 523,063

[22] Filed: May 14, 1990

[51] Int. Cl.$^5$ ............................................ C10M 105/72
[52] U.S. Cl. .................................. 252/48.2; 252/46.6; 252/47; 252/47.5; 252/48.6; 568/22; 568/26
[58] Field of Search ................... 252/46.4, 46.6, 48.2; 568/22, 26

[56] References Cited

FOREIGN PATENT DOCUMENTS

| 0058134 | 8/1982 | European Pat. Off. | 568/22 |
| 1021065 | 5/1965 | Japan | 568/22 |
| 222155 | 9/1988 | Japan | 568/22 |

*Primary Examiner*—Price Willis, Jr.
*Assistant Examiner*—M. Nuzzolillo
*Attorney, Agent, or Firm*—Burgess, Ryan & Wayne

[57] ABSTRACT

This invention relates to additives to lubricants with antiwear and extreme-pressure effect consisting of asymmetric dihydrocarbyl polysulphides containing a hydrocarbyl polysulphide group $R\text{-}S_x\text{-}$ in a vicinal position of a secondary or tertiary alcohol, and to lubricating compositions containing these additives. The additives are prepared by reaction of a basic salt of a hydrocarbyl (poly)sulphide either with a compound containing at least one epoxy group or with an alpha-hydroxylated organic thiosulphate.

19 Claims, No Drawings

SULPHUR-CONTAINING ADDITIVES TO LUBRICANTS WITH ANTIWEAR AND EXTREME-PRESSURE EFFECT AND THE PROCESSES FOR THEIR PREPARATION AND COMPOSITIONS CONTAINING THE SAID ADDITIVES

BACKGROUND OF THE INVENTION

1) Field of the Invention

The present invention relates to organic sulphur compounds which can be employed as antiwear and extreme-pressure additives to lubricants, to the synthesis of these compounds and to lubricating compositions containing the said compounds.

2) Description of the Related Art

Extreme-pressure additives are employed chiefly in oils for industrial or motor vehicle gear drives or for specific lubricants for machining metals. These compounds, which generally contain sulphur, chlorine, phosphorus or nitrogen, act by forming a surface layer which prevents the formation of local microwelds. These microwelds are produced by high-amplitude heat effects which appear between two surfaces moving relative to each other under high stresses.

The extreme-pressure additives currently employed can be classified into four groups.

The first group concerns the products resulting from the reaction of alcohols, phenols, olefins and/or hydrocarbon compounds containing sulphur, chlorine and nitrogen atoms with phosphorus derivatives such as phosphorus pentasulphide. These products are described, for example, in U.S. Pat. No. 4,058,463. The extreme-pressure effect of these sulphur-containing and phosphorus-containing additives is generally insufficient, but they have advantageous additional properties. In particular, they are antioxidants and are noncorrosive.

The second group concerns the products formed by reaction of mono- or polyunsaturated olefins or of aromatic compounds which are optionally substituted by alkyl chains, or by hydrocarbon chains containing heteroatoms such as sulphur, chlorine, phosphorus or nitrogen, or else fatty acid esters with chlorine-containing sulphur compounds ($SCl_2$, $S_2Cl_2$, R-S-Cl).

The product obtained is in some cases treated with an alkali metal hydroxide, a sodium mercaptide or a sodium polysulphide to reduce the residual chlorine content. These products are described, for example, in U.S. Pat. Nos. 4,204,269, 4,198,305, 4,097,387, 3,925,414 and 3,844,964 and French Pat. No. 2,404,042.

French Pat. No. 2,588,881 recommends adding an alkenyl chloride before the treatment with an alkali metal polysulphide to improve the solubility of the final products in the oil.

French Pat. No. 2,605,328 recommends the subsequent treatment with an organic polysulphide as a replacement for sodium polysulphide to improve the solubility of the final products in mineral and synthetic oils.

The products obtained according to these processes have medium to high sulphur contents (up to 50%), endowing them with excellent extreme-pressure properties, but they are frequently corrosive. One of the major disadvantages in the synthesis of these products concerns the final washing stages, which increase the cost of the process. These products generally contain a little residual chlorine, and this may limit their use in some applications.

The third group comprises the products resulting from the reaction of mono- or polyunsaturated olefins, unsaturated fatty acid esters or of hydrocarbon compounds containing heteroatoms such as sulphur, chlorine, phosphorus or nitrogen with elemental sulphur or a mixture of elemental sulphur and of hydrogen sulphide, in the presence or in the absence of catalyst. There are, for example, known processes using the reaction of isobutylene or of $C_3$-$C_8$ olefins with sulphur, as mentioned in U.S. Pat. Nos. 4,119,850, 4,119,545 and 3,899,475.

The fourth group comprises the products of addition of inorganic sulphur derivatives to epoxides.

German Pat. No. DE 36 04,793 claims the preparation of antiwear and extreme-pressure additives by condensation of epoxides which are preferably obtained by epoxidation by alpha-olefins containing 6 to 20 carbon atoms with a sodium polysulphide such as $Na_2S_2$ or $Na_2S$. The products generally contain from 15 to 30% of sulphur and are noncorrosive towards noble metals.

U.S. Pat. No. 3,064,056 recommends the preparation of bis(beta-hydroxyalkyl) di- or trisulphides by reaction of an epoxide with elemental sulphur in the presence of basic catalyst.

All these products have a symmetrical structure, and this considerably limits the number of possible variants.

SUMMARY OF THE INVENTION

We have now found a new group of sulphur-containing additives of asymmetric structure. This asymmetric structure makes it possible to adjust much more finely both the solubility of these products in the oil and their antiwear and extreme-pressure performance.

For this purpose, the new sulphur-containing additives to lubricants with antiwear and extreme-pressure effect are characterized in that they consist of asymmetric dihydrocarbyl polysulphides containing a hydrocarbyl polysulphide group $R-S_x$- in a vicinal position of a secondary or tertiary alcohol.

R denotes an aliphatic radical, generally $C_1$-$C_{18}$ and preferably $C_1$-$C_{14}$, which may contain one or more heteroatoms such as oxygen, sulphur, phosphorus or nitrogen, an aromatic radical optionally substituted by one or more aliphatic radicals which may contain heteroatoms or a heterocyclic radical containing at least one heteroatom chosen from sulphur, oxygen or nitrogen.

The value of x may vary between 2 and 10 inclusive and preferably between 2 and 6 inclusive.

The $R-S_x$- groups originate from corresponding aliphatic, aromatic or heterocyclic mercaptans.

The additional sulphur atoms are introduced with the aid of inorganic sulphur derivatives such as elemental sulphur or alkali metal thiosulphates like sodium or ammonium thiosulphate.

DESCRIPTION OF THE PREFERRED EMBODIMENT

According to the direct method of implementing the invention, a basic salt of an organic polysulphide $R-S_xM$ is prepared by reaction of the basic salt of a mercaptan, R-SM with at least one equivalent of elemental sulphur, and this polysulphide is then reacted with an epoxide.

In formula R-SM, R has the abovementioned meaning, while M denotes an alkali or alkaline-earth metal or a monovalent group, like NH, corresponding to an inorganic base MOH.

Another process consists in first preparing an alpha-hydroxylated organic thiosulphate by addition of an alkali metal thiosulphate to a compound containing at least one epoxy group. In a second step the alpha-hydroxylated organic thiosulphate reacts with the basic salt of a mercaptan R-SM or of an organic polysulphide R-S$_x$M where R, M and x have the abovementioned meaning.

Among the aliphatic mercaptans which can be employed for preparing the products of the invention there may be mentioned methyl mercaptan, ethyl mercaptan, propyl mercaptan, n-butyl mercaptan, isobutyl mercaptan, tert-butyl mercaptan, tert-amyl mercaptan, tert-nonyl mercaptan, tert-dodecyl mercaptan and benzyl mercaptan. Among the aliphatic mercaptans containing one or more heteroatoms we mention mercaptoethanol, 3-mercapto-1,2-propanediol, mercaptoacetic or thioglycolic acid and mercaptopropionic acid.

Among aromatic mercaptans we mention phenyl mercaptan or thiophenol, tolyl mercaptans and ortho-thiobenzoic acid or thiosalicylic acid.

Among heterocyclic mercaptans we mention 2-mercaptoimidazole, 2-mercaptomethylimidazole, 2-mercaptobenzimidazole, 2-mercaptobenzoxazole, 2-mercaptopyridine, 4-mercaptopyridine, 2-mercaptothiazole, 2-mercaptothiazoline, 2-mercapto-5-methyl-1,3,4-thiadiazole and 3-mercapto-4-methyl-1,2,4-triazole.

The compounds containing at least one epoxy group have an acyclic or cyclic hydrocarbon structure.

The epoxy groups may be in a terminal position or in the middle of the acyclic structures, the difference being of no importance. In fact, it is known that the opening of epoxides in a terminal position by a mercaptan or an alkyl polysulphide produces secondary or tertiary alcohols. Only ethylene oxide, whose opening under these conditions gives a primary alcohol, is excluded from the field of the invention.

Among acyclic compounds containing at least one epoxy group in a terminal position there may be mentioned 1,2-epoxypropane, 1,2-epoxybutane, 1,2-epoxyhexane, 1,2-epoxyoctane, 1,2-epoxydodecane and epoxystyrene or diepoxides, like 1,2,3,4-diepoxybutane.

Among the acyclic compounds containing epoxy groups in the middle of a chain there may be mentioned epoxides of unsaturated fatty acids such as epoxidized oleic acid or methyl oleate, epoxidized methyl linoleate or epoxidized soya oil.

Among cyclic epoxides there may be mentioned 1,2-epoxycyclohexane.

It may be advantageous to employ compounds which contain a functional group such as a halogen, an alcohol or an ether in a vicinal position relative to the epoxide. There may be mentioned epichlorohydrin, epibromohydrin and alkyl glycidyl ethers like n-butyl glycidyl ether, 2-ethylhexyl glycidyl ether or phenyl glycidyl ether.

The basic salts of the mercaptans may be obtained by reaction of a mercaptan with an inorganic base MOH, preferably in alcoholic medium. Sodium hydroxide, potassium hydroxide or aqueous ammonia are most commonly employed. The alcoholic medium may contain at least one aliphatic monoalcohol, such as methanol, ethanol or isopropanol. The reaction is generally carried out at a temperature of 20 to 100° C.

The basic salts of the mercaptans may be converted into polysulphides by reaction with one or more equivalents of elemental sulphur.

According to the direct method of implementation, the polysulphides in the form of their basic salts react with the epoxide in alcoholic or hydroalcoholic medium at a temperature of between approximately 20 and 120° C. and preferably between 50 and 70° C. Methanol, ethanol or isopropanol is preferably employed among the alcohols. The reaction time is generally between 0.5 and 5 hours. A period of approximately one hour is generally sufficient.

At the end of reaction the products are extracted with an organic solvent such as toluene or xylenes, and ar isolated after evaporation of the solvent.

According to the other process, an alphahydroxylated organic thiosulphate is prepared first by reaction of an alkali metal thiosulphate with an epoxide.

A mixture of sodium thiosulphate and ammonium thiosulphate in an alcoholic or hydroalcoholic medium is generally employed. The reaction time varies between approximately 1 and 5 hours and the temperature between 20 and 100° C. The paste obtained after the evaporation of the solvents is purified by redissolving and reevaporation.

In a second step the alpha-hydroxylated organic thiosulphate reacts with the basic salt of the mercaptan or with the basic salt of the organic polysulphide, in an alcoholic or hydroalcoholic medium, at a temperature of between 20 and 120° C., preferably between 50 and 70° C. Methanol, ethanol or isopropanol is preferably employed. The reaction time is between 0.5 and 5 hours, a period of an hour being generally sufficient. At the end of reaction the products are extracted with an organic solvent such as toluene or xylenes.

Groups R-S$_x$- where x=2 are introduced by reaction with the mercaptans. The use of the corresponding polysulphides allows the number of sulphur atoms to be increased to the desired value.

The organic sulphur compounds according to the invention are employed as additives with an antiwear and extreme-pressure effect for lubricants.

By varying the structure of the mercaptans and epoxides employed and the number of sulphur atoms introduced into the molecule it is possible to adjust the solubility in oils and the antiwear and extreme-pressure effect. In most cases the solubility is complete.

A first application of the additives of the invention is more particularly concerned with the formulation of oils intended for the lubrication of gear drives. The base oils may be mineral or synthetic in origin.

The synthetic oils include especially olefin oligomers such as tri-, tetra- and pentamers of 1-decene, obtained by oligomerization in the presence of Lewis acids. Other alpha-olefins can, of course, be employed, for example C$_6$-C$_{14}$ alpha-olefins.

It is also possible to employ alkylbenzenes such as mono- and dialkylbenzenes, or synthetic esters originating from mono- or polycarboxylic acids (such as sebacic acid, fatty acids, and the like) and from monoalcohols or polyols (such as 2-ethylhexanol, trimethylolpropane, and the like).

The additives according to the invention may be added to the lubricating oils in concentrations ranging, for example, from 0.5 to 10 mass %.

These additives may be employed in combination with phosphorus-containing additives such as metal dialkyl- or diaryldithiophosphates, phosphites and organic phosphates.

Other conventional additives may be added, such as antioxidants, rust inhibitors, copper passivators, foam suppressors or friction reducers, in the usual proportions.

A second application as extreme-pressure additives for lubricants is concerned more particularly with the formulation of oils intended for the working of metals (cutting, forming, and the like).

In this application the additive concentration employed is generally from 0.1 to 20% and preferably from 0.5 to 5 mass % relative to the lubricating oil. Other conventional additives may be added in this application, such as chlorinated paraffins in a proportion corresponding, for example, to 2–10 mass % of chlorine relative to the lubricating oil.

The following examples illustrate the invention; they must not be considered as limiting in any manner.

EXAMPLE I a) 300 ml of water, 125 g (0.5 moles) of sodium thiosulphate and 75 g (0.5 moles) of ammonium thiosulphate are introduced with stirring and at room temperature into a 1000 ml conical. When the whole has become homogeneous, 72 g (1 mole) of 1,2-epoxybutane and 250 ml of ethanol are added. After heating for an hour under reflux the two-phase solution becomes homogeneous and clear. Heating is kept up for approximately 2 h 30 min (corresponding to the time at the end of which no further release of ammonia is observed).

After evaporation of the solvents, the paste obtained is taken up with ethanol and the alcohol is then evaporated off. A white powder (202 g) is obtained, which is characterized by elemental analysis. C 22.91 (theory 23.1), H 4.44 (theory 4.30), Na 11.3 (theory 11.06)

b) 74 ml of 95% ethanol, 4.4 g of sodium hydroxide pellets and 9 g (0.1 mole) of tert-butanethiol are introduced into a 250-ml reactor. The whole is heated to 40° C. with stirring for 30 min. 60 ml of an aqueous solution containing 23 g of the alpha-hydroxy-s-butyl thiosulphate prepared in 1(a) are added by means of a dropping funnel and the solution is then heated to reflux for an hour.

The product is then extracted with 3×30 ml of toluene. After drying the organic phase over magnesium sulphate and then evaporating off the solvent 18 g of yellow-coloured odourless oil containing 32% of sulphur are recovered.

EXAMPLE II 50 ml of methanol and 4.8 g of sodium hydroxide pellets are introduced into a 250 ml reactor; the mixture is heated to about 60° C. until the sodium hydroxide has dissolved. 10.8 g of tert-butyl mercaptan are then added dropwise, the temperature being kept at 60° C. for 30 minutes after the end of addition.

8,7 g of 1,2-epoxybutane are then introduced (a 10° C. temperature rise is observed). The solution is kept refluxing for approximately 30 min and 200 ml of toluene are then added. The extracted organic phase is washed with water and then dried over magnesium sulphate. After filtration and evaporation of the solvent 18 g of an odourless and colourless oil are recovered. The sulphur content is equal to 33.5% (theory 33%).

EXAMPLE III 50 ml of methanol and 4 g of sodium hydroxide pellets are introduced into a 250 ml reactor; the mixture is heated to 50° C. until the sodium hydroxide has dissolved. 9 g of tert-butanethiol are then added dropwise, the temperature being kept at 60° C. for approximately 30 minutes after the end of addition, and 6.4 g of flowers of sulphur are then added to this homogeneous solution. The temperature is maintained for an additional 30 minutes. 7.3 g of 1,2-epoxybutane are then added dropwise (the temperature increases by 10° C.). The heating is continued for 30 minutes. 150 ml of toluene are then added. The extracted organic phase is washed with 2×50 ml of water and is then dried over magnesium sulphate. After filtration and evaporation of the solvent 20 g of an oil containing 42.5% of sulphur (theory 42%) are recovered.

EXAMPLE IV

The procedure is as in the preceding example, but with sodium hydroxide being replaced with 10 ml of a 20% strength aqueous ammonia solution. 17.3 g of an oil containing 52% of sulphur are obtained.

EXAMPLE V

After dissolving 2.1 g (0.05 moles) of sodium hydroxide, 11 g (0.05 moles) of tert-dodecyl mercaptan are introduced into a reactor containing 100 g of 95% ethanol. The mixture is heated under reflux until it becomes homogeneous, and is then cooled to room temperature before adding 11.6 g of the organic thiosulphate prepared according to Example Ia. The solution is heated under reflux for an hour. After cooling, 200 ml of water are added to dissolve the sodium sulphite. The organic phase is separated off and the aqueous phase is extracted with 2×30 ml of toluene and 30 ml of ethyl ether. The organic phases are combined and are dried over magnesium sulphate. After evaporation of the solvents 15.5 g of an oil (theory 16.5 g) containing 22% of sulphur are recovered.

EXAMPLE VI

The procedure is as in Example II, employing 11 g (0.05 moles) of tert-dodecyl mercaptan, 21 g of sodium hydroxide, 1.6 g of flowers of sulphur and 3.6 g of butene oxide.

15 g of an oil containing 21.2% of sulphur are recovered.

EXAMPLE VII

The procedure is as in Example I, but with tert-butanethiol being replaced with n-butanethiol. An oil containing 35% of sulphur (theory 32%) is obtained in a 75% yield.

EXAMPLE VIII

The extreme-pressure properties of the products of the invention are evaluated in this example, by starting with a 350 Neutral Solvent mineral oil containing 1% of the additives of the invention, using a 4-ball machine according to the ASTM method D 2783.

| Additive (1% in 350 N) | Seizing load | Welding load | Load-wear index |
|---|---|---|---|
| base alone | 60 | 126 | 22 |
| Ib | 80 | 250 | 32 |

-continued

| Additive (1% in 350 N) | Seizing load | Welding load | Load-wear index |
|---|---|---|---|
| II | 80 | 250 | 33.7 |
| III | 126 | 315 | 50.1 |
| IV | 100 | 315 | 49.5 |
| V | 100 | 250 | 32 |
| VI | 100 | 250 | 35 |
| VII | 100 | 250 | 33.7 |

These results show that the additives according to the invention produce an appreciable increase in the load-wear index, and in the seizing and welding loads. Bearing in mind these performances, these additives can be advantageously employed for the formulation of extreme-pressure oil for industrial or motor vehicle gear drives.

EXAMPLE IX

The corrosive effect of the additives of the invention towards copper is evaluated in this example, using tests of corrosion of a copper strip by solutions of 350 Neutral Solvent mineral oil containing 3% of additive of the invention and 300 ppm of benzotriazole. The solutions are heated to 100° C. for 3 hours.

The results obtained are collated in the table below. They are expressed as a classification comprising a number followed by a letter specifying the corrosion hue of the copper strip.

| Additive (3% in 350 NS) | 3 h at 100° C. |
|---|---|
| II | 1b |
| III | 1b |
| IV | 1b |

Products exhibiting a classification lower than 3 are particularly suited for the formulation of oils for gear drives.

We claim:

1. Sulphur-containing additives to lubricants, with anti-wear and extreme-pressure effect, comprises of asymmetric polysulphides containing a polysulphide group R-$S_x$-, where R denotes a $C_1$-$C_{18}$ aliphatic radical and x varies between 2 and 10 in a vicinal position of a secondary or tertiary alcohol.

2. Additives according to claim 1, wherein R denotes a $C_1$-$C_{18}$ aliphatic radical which contains one or more heteroatoms.

3. Additives according to claim 1, wherein R denotes a $C_1$-$C_{14}$ aliphatic radical which contains one or more heteroatoms selected from the group consisting of oxygen, sulphur, phosphorus and nitrogen.

4. Additives according to claim 1, wherein the value of x varies between 2 and 6.

5. Process for the preparation of additives according to claim 1, which comprises the steps of:
(a) reacting a basic salt of a mercaptan R-SM with at least one equivalent of elemental sulphur to produce a basic salt of a polysulphide R-$S_x$M, wherein R denotes a $C_1$-$C_{18}$ aliphatic radical, x varies between 2 and 10, and M denotes an alkali or alkaline-earth metal or a monovalent group corresponding to an inorganic base MOH,
(b) reacting said polysulphide with a compound containing at least one epoxy group, and
(c) recovering said additives.

6. Process for the preparation of additives according to claim 1, which comprises the steps of:
(a) reacting an alkali metal thiosulphate with a compound containing at least one epoxy group to form an alpha-hydroxylated organic thiosulphate compound,
(b) reacting said compound with a basic salt of a mercaptan R-SM or an organic polysulphide R-$S_x$M, wherein R denotes a $C_1$-$C_{18}$ aliphatic radical, x varies between 2 and 10, and M denotes an alkali or alkaline-earth metal or a monovalent group corresponding to an inorganic base MOH, and
(c) recovering said additives.

7. Process according to claim 5, wherein the basic salts of mercaptans are obtained by reaction of a mercaptan with an inorganic base selected from the group consisting of sodium hydroxide, potassium hydroxide and aqueous ammonia.

8. Process according to claim 5, wherein the basic salts of organic polysulphides are obtained by reaction of basic salts of mercaptans with at least one equivalent of elemental sulphur.

9. Process according to claim 5, wherein the mercaptan is an aliphatic mercaptan selected from the group consisting of methyl mercaptan, ethyl mercaptan, propyl mercaptan, n-butyl mercaptan, isobutyl mercaptan, tert-butyl mercaptan, tert-amyl mercaptan, tert-nonyl mercaptan, and tert-dodecyl mercaptan.

10. Process according to claim 5, wherein the aliphatic mercaptan contains one or more heteroatoms, and is selected from the group consisting of mercaptoethanol, 3-mercapto-1,2-propanediol, mercaptoacetic or thioglycolic acid and mercaptopropionic acid.

11. Process according to claim 5, wherein the compound containing at least one epoxy group has an acyclic hydrocarbon structure containing the epoxy group(s) in a terminal position, and is selected from the group consisting of 1,2-epoxypropane, 1,2-epoxybutane, 1,2-epoxyhexane, 1,2-epoxyoctane, 1,2-epoxydodecane, epoxystyrene and 1,2,3,4-diepoxybutane.

12. Process according to claim 5, wherein the compound containing at least one epoxy group has an acyclic hydrocarbon structure containing the epoxy group(s) in the middle of a chain, and is selected from the group consisting of epoxidized oleic acid, epoxidized methyl oleate, epoxidized methyl linoleate and epoxidized soya oil.

13. Process according to claim 5, wherein the compound containing at least one epoxy group has a cyclic hydrocarbon structure.

14. Process according to claim 5, wherein the compound containing at least one epoxy group contains a functional group selected from the group consisting of a halogen, an alcohol and an ether, in a vicinal position relative to the epoxy group.

15. Process according to claim 5, wherein the compound containing at least one epoxy group is selected from the group consisting of epichlorohydrin, epibromohydrin, n-butyl glycidyl ether, 2-ethylhexyl glycidyl ether and phenyl glycidyl ether.

16. Lubricating composition with antiwear and extreme-pressure effect useful for the lubrication of gear drives, and which contains a mineral or synthetic lubricating oil and 0.5 to 10 mass % of an additive according to claim 1.

17. Lubricating composition according to claim 16, which contains additives selected from the group consisting of phosphorus-containing additives, antioxidants, rust inhibitors, copper passivators, foam suppressors and friction reducers.

18. Lubricating composition with antiwear and extreme-pressure effect useful for formulations for working metals, and which contain a mineral or synthetic lubricating oil and 0.1 to 20 mass % of an additive according to claim 1.

19. Lubricating according to claim 18, which contains chlorinated paraffins.

* * * * *